United States Patent [19]

Hammond et al.

[11] Patent Number: 4,629,706

[45] Date of Patent: Dec. 16, 1986

[54] METHOD FOR DETERMINING ALLERGIC SENSITIVITY

[75] Inventors: Michael D. Hammond, Postcombe; William J. A. Taylor, Windsor, both of England

[73] Assignee: Miles Laboratories, Inc., Elkhart, Ind.

[21] Appl. No.: 622,722

[22] Filed: Jun. 20, 1984

Related U.S. Application Data

[63] Continuation-in-part of Ser. No. 344,478, Feb. 1, 1982, abandoned.

[51] Int. Cl.$^4$ .............................................. G01N 33/49
[52] U.S. Cl. ..................................... 436/513; 436/34; 436/50; 436/63; 436/69; 436/70; 436/517; 73/64.1; 422/73; 424/91; 435/13
[58] Field of Search ........................... 73/64.1; 422/73; 424/91; 435/13; 436/34, 50, 63, 69, 70, 513, 517

[56] References Cited

U.S. PATENT DOCUMENTS

3,720,760  3/1973  Bennich et al. .......................... 435/7
4,581,920  4/1986  Völkl ..................................... 73/64.1

FOREIGN PATENT DOCUMENTS

0660668  5/1979  U.S.S.R. ............................... 436/513

OTHER PUBLICATIONS

J. Immunol., 115:525-532 (1975), R. N. Pinckard, et al., "IgE-Induced Blood Coagulation Alterations in the Rabbit: Consumption of Coagulation Factors XII, XI & IX In Vivo".

Clinical Research, 25:361A (1977), A. P. Kaplan, et al., "Human Anaphylaxis: A Study of Mediator Systems".

J. Immunol., 123:2835-2841 (1979), L. M. McManus, et al., "Platelet Activating Factor (PAF) Induced Release of Platelet Factor 4 (PF4) In Vitro & During IgE Anaphylaxis in the Rabbit".

J. Lab. Clin. Med., 89(6):1306-1313 (1977), J. Blakely, et al. "An In Vitro Measurement of Bleeding Time".

J. Lab. Clin. Med., 81:291 (1973), D. A. Levy, et al., "A Microassay for Studying Allergic Histamine Release from Human Leukocytes Using an Enzymic-Isotopic Assay for Histamine".

Primary Examiner—Robert J. Warden
Assistant Examiner—Robert Benson
Attorney, Agent, or Firm—Edward P. Gray

[57] ABSTRACT

A method for determining allergenic sensitivity of a mammal is disclosed. The method involves measuring the time required for hemostasis of a blood sample with an allergen in the presence of a blood clotting inhibitor and comparing the time required for hemostasis in the presence of a blood clotting inhibitor and the absence of the allergen. The sensitivity to the allergen is determined by determining the difference in time required for hemostasis.

6 Claims, No Drawings

METHOD FOR DETERMINING ALLERGIC SENSITIVITY

CROSS-REFERENCE

This application is a continuation-in-part of our co-pending application, Ser. No. 344,478, filed Feb. 1, 1982 now abandoned.

BACKGROUND OF THE INVENTION

1. Field of the Invention

The basic function of the organs, cells and molecules that comprise the immune system is to recognize and to eliminate foreign substances from the body. These foreign substances are eliminated by reaction between the foreign substance and antibodies which are formed in response to the substance. In general, this function is performed efficiently and without detriment to the host. However, in hypersensitive individuals, disturbances can occur which can lead to pathogenic disorders such as, an uncontrolled response, for example, allergic disorders.

Hypersensitive individuals undergo an "altered state" as a result of contact with the antigens from an allergen, leading to the formation of antibodies thereto. Subsequent contact with one of those antigens or a structurally similar substance can evoke in a hypersensitive individual a pathological reaction, due to the presence of such antibodies. When these individuals inhale or ingest the offending antigen, a prominent and common manifestation includes hay fever, asthma, urticaria ("hives") or dermatitis. The tendency to develop this form of allergy is hereditable.

Allergic responses are involved with the production within an individual of tissue-sensitizing IgE antibodies. These IgE antibodies have a high affinity for receptors on cells present in various body tissues. The receptors are on mast cells which are found in close association with capillaries in connective tissues throughout the body and on basophilic leukocytes (blood cells). Mast cells and basophils contain pharmacologically-active mediators or spasmogens, such as histamine, serotonin (5-hydroxytryptamine) and kinins (basic peptides) concentrated in cytoplasmic granules. Contact of the IgE antibodies, which are fixed to mast cells and basophils, with antigens can trigger cross-linking of the IgE antibodies. In turn, this cross-linking causes degranulation of mast cells and basophils, which release the chemical mediators and produce manifestations of the allergic response referred to earlier.

Allergy diagnosis can be accomplished in numerous ways. A frequency used method involves studying the patient's history, i.e., recent exposure to various allergens, and based on a decision regarding the identity of the suspected allergen, injecting small amounts of the suspected allergen into the skin, and examining the injected site for a reaction which is characterized by erythema and wheal formation and associated pruritus. This method is quick and easy for the clinician and considered to be a reliable indication of allergen sensitivity because it is conducted in vivo. However, this method can involve considerable patient discomfort, is difficult to conduct with children, can expose an extremely hypersensitive patient to danger, and may be difficult to interpret in patients with severe dermatitis.

When allergy to foods is suspected, dietary exclusion tests can be utilized. These tests are not convenient for the patient and can involve a lengthy procedure.

In vitro tests which involve specific binding assay methods are also used. A typical specific binding assay procedure is the determination of IgE antibodies in the blood of a hypersensitive individual. U.S. Pat. No. 3,720,760 is directed to a technique which measures allergen-specific IgE levels in serum by the radioallergosorbent test (RAST). This type of in vitro test is expensive and requires a sophisticated laboratory in addition to requiring about 36 hours to complete.

DESCRIPTION OF THE PRIOR ART

*J. Immunol.*, 115:525–532 (1975) describes a study involving rabbits, of IgE-induced blood coagulation alterations after antigen challenge, and its initiation of blood coagulation. The research involved demonstrated a decrease in the functional levels of blood clotting factors XII, XI, and IX and in the clottable fibrinogen concentration (Factor I) and a prolongation of the partial thromboplastin time, i.e., an increase in the time required for blood coagulation. The authors state that the study is the first reported documentation of the involvement of specific IgE antibody in the initiation of blood coagulation. *Clin. Res.*, 25:361A (1977) describes a study of immunotherapy for insect hypersensitivity in man. The study involved 20 patients sensitive to insect venom. The patients were challenged with increasing doses of venom. There were 3 cases of anaphylactic shock and 12 cases of urticaria. In the 2 patients with the most severe anaphylactic shock, evidence of intravascular coagulation was observed, with a diminution of blood clotting factors V, VIII and fibrinogen. In the patient with the mildest anaphylactic shock, as well as the patients with urticaria, no significant changes in the coagulation system were evident, even though the urticaria response indicated allergen sensitivity. The authors concluded that in even severe episodes of anaphylactic shock, in some instances the coagulation system was not activated.

*J. Immunol.*, 123:2835–2841 (1979) describes studies conducted involving rabbits, of a basophil-derived platelet activating factor (PAF), which induces the release of a platelet factor 4 (PF4) which is an intrinsic platelet constituent involved in inflammatory reactions. The studies decumented that during IgE anaphylaxis the antigen stimulates circulating IgE-sensitized basophils to release PAF, which causes intravascular platelet aggregation.

None of the references described above disclose or suggest a diagnostic test for allergic hypersensitivity involving contacting a patient's blood with an allergen and determining the effect on the time required for hemostasis of the blood. The *J. Immunol.* (115) article describes an increase in the time required for blood coagulation in rabbits following antigen challenge; the *Clin. Res.* article indicates that in known hypersensitive individuals, exposure to the allergen does not correlate with a decrease in blood coagulation factors, even among patients who undergo anaphylactic shock. There is no disclosure of the effect on hemostasis time of the blood.

SUMMARY OF THE INVENTION

The present invention is directed to a method for determining the allergic sensitivity of a mammal. The method involves the steps of contacting a sample of blood from the mammal with an allergen in the presence of a blood clotting inhibitor and measuring the time required for hemostasis. As a control, a sample of blood from the animal is contacted with a blood clotting inhibitor in the absence of the allergen, and the time required for hemostasis is measured. The sensitivity of the allergen is determined by the difference in time required for hemostatis.

DESCRIPTION OF THE INVENTION

The present invention relates to the determination of allergic sensitivity to specific allergens in allergic individuals. Allergens can be as diverse as pollens, chemicals, insect venom and food, for example, milk, cereal and fish, such as cod, shellfish and haddock. Allergens include various antibiotics such as penicillin; *Candida albicans*, insulin, ovalbumin, lactalbumin, secale, bermuda grass pollen, timothy grass pollen, orchard grass pollen (cocksfoot grass pollen), combination of grass pollens, ragweed pollen, ragweed antigen E, birch tree pollen, bee venom, snake venom, horse dander, cat epithelium, dog epithelium, haddock, house dust mite, *Chrysanthemum leucanthemum*, *Alternaria tenuis*, trypsin, chymotrypsin, dry rot, baker's yeast, tetanus toxoid, diphtheria toxin, and ficin among others. Regardless of the identity of the allergen, it is theorized that the underlying mechanism of allergen response is the same.

When blood vessels in mammals are cut, platelets adhere to exposed collagen and to each other to form aggregates resulting in hemostasis, i.e., the arrest of bleeding. Hemostasis therefore measures the "bleeding time" of a mammal. Hemostasis is a result of a dynamic process involving the interaction of several elements, among them platelets, plasma coagulation factors and the blood vessel walls. Hemostasis can be simulated as described hereinafter.

Formation of a hemostatic aggregate is an early stage of the complex process involved in blood coagulation. Blood coagulation includes the conversion of prothrombin to thrombin and the conversion by thrombin of fibrinogen into fibrin and formation of blood clots. This final formation of a blood clot is referred to as "coagulation". Induction of blood clotting by allergens has been determined to be a relatively inconsistent indicator of allergen sensitivity. Clotting of blood in the present method is in fact undesirable.

The invention involves mixing a blood sample with a clotting inhibitor to prevent blood clotting. The amount of clotting inhibitor required is easily determined by routine testing. It has been determined that 5 International Units of heparin/ml of blood sample is sufficient. The time required for hemostasis is then measured by simulating blood flow, bleeding, and occurrence of hemostasis, in a mammal. In order to determine the effect of the presence of a selected allergen, hemostasis is measured in the presence of the allergen, and in the absence of the allergen, as a control. The allergen can be used as a liquid extract, solid allergenic material, or can be coupled to a carrier which is a water insoluble synthetic matrix, as taught in U.S. Pat. No. 3,720,760 described hereinafter. For example, carbohydrate matrices such as agarose and cellulose, paper discs and the walls of polystyrene test tubes can be used as the inert carrier. A decrease in the time required for hemostasis was found to correlate with allergic sensitivity.

The identity of the clotting inhibitor is not critical. Suitable clotting inhibitors include heparin, calcium citrate, sodium citrate, calcium oxalate, sodium oxalate and ethylenediamine tetracetic acid.

As described hereinafter, the time required for hemostasis to occur can be determined using apparatus which includes a circuit of plastic tubing having a section of tubing of reduced bore size leading to and from a reservoir. The reduced bore section has a hole of pre-determined diameter, e.g., 0.013 inch. A blood sample, mixed with a clotting inhibitor, is placed into the reservoir. When the attached plastic tubing is contacted with peristaltic rollers, this circulates the blood in a pulsatile fashion. When the blood reaches the length of smaller bore size, the velocity of the blood increases, forcing blood out of the hole, as well-defined droplets. The time required for hemostasis, due to the formation of a hemostatic aggregate, is determined by measuring the decrease in the rate of droplet formation, or measuring the time required for the hole to become occluded due to the formation of a hemostatic aggregate.

Suitable apparatus for use in the instant claimed method is described in *J. Lab. Clin. Med.*, 89(6): 1306–1313 (1977) of is commercially available from Payton Associates, Buffalo, N.Y. 14202. Other methods of measuring hemostatic aggregate formation can be used.

In order to establish a positive correlation between the method of the present invention (i.e., hemostasis time) and allergenic sensitivity, the following study was conducted.

Forty-four adults were selected and blocked into three groups: grass sensitive; non-grass sensitive; and non-atopic (i.e., control). The distribution into a particular group was done on the basis of a clinical history taken for each person utilizing a standard allergy case history questionnaire. Each person was tested for allergenic sensitivity to Timothy Grass Pollen Extract (hereinafter referred to as "allergen") by three tests commonly used for allergy sensitivity diagnosis: skin prick test; radioallergosorbent test (RAST); and allergen-induced histamine release test. Each person was also tested for hemostasis time according to the method of the present invention. The techniques utilized in each of the four tests are set forth below, and the comparative results obtained are summarized in Table I.

SKIN PRICK TEST

Each patient's skin was pricked with a sterile lancet through a drop of a glycerinated solution of allergen; an allergic reaction results in symptoms such as reddening of the skin and the formation of a wheal and flare. Skin prick tests were conducted by administering about a 100 microliter amount of allergen extract to each patient followed by a measurement of the resultant wheal (if any) in millimeters (mm).

RAST TEST

Blood serum samples from each patient were tested for the presence of antibodies directed against the allergen by the method described in U.S. Pat. No. 3,720,760. Briefly, the method involves coupling the allergen to a water insoluble polymer and contacting the bound allergen with a blood sample. The allergen can be coupled to a water insoluble synthetic matrix by washing the matrix with distilled water and adding cyanogen bromide to the matrix while maintaining the pH at about 11 with NaOH, to "activate" the matrix. The activated matrix is washed with a coupling buffer, e.g., 0.1M $NaHCO_3$ and 1.0M NaCl, at a pH of 8.5. The allergen is TABLE I-continued

| PATIENT NO. | SKIN PRICK TEST[a] | RAST[b] | ALLERGEN-INDUCED HISTAMINE RELEASE[c] | % BTA[d] |
|---|---|---|---|---|
| 37 | 0 | 13.5 | 0 | 112.9 |
| 41 | 0 | 8 | 0 | 106.4 |

[a]Mean wheal in millimeters from two trials.
[b]ng/ml of IgE antibody specific to Timothy Grass Pollen Extract.
[c]Percent of total histamine released at 0.1 pnu/ml of allergen.
[d]Mean value for two trials for each patient.
[e]Patient No. 21 exhibited a positive skin response to a negative control (i.e. glyero-saline)

From the data shown in Table I, it may be readily observed that those patients who were blocked into the grass-sensitive group as a result of their clinical history generally gave a positive response to the Skin Prick Test while the nonsensitive and control groups gave negative results. Further, from the Allergen-Induced Histamine Release Test a tendency was seen for the grass-sensitive group to undergo a greater release of histamine than those patients in the non-grass sensitive and control groups. Similarly, RAST scores were generally higher for patients in the grass-sensitive group than for patients in the other two groups. Consistent with the results obtained by these known diagnostic tests, the percent bleeding time in the presence of antigen (% BTA) was generally decreased for patients in the grass-sensitive group and remained generally unchanged or increased for patients in the other two groups, thereby exhibiting a positive correlation between the method of the present invention and known diagnostic test methods.

Because the data set forth in Table I do not lend themselves to direct comparative analysis, statistical methods were employed to obtain a correlation between the results of each of the four test methods.

The Spearman coefficient of rank correlation, a standard statistical method for analyzing any continuous distribution having ranked values, was calculated for the four tests described above. Each of the forty-three patients (patient No. 21 was not included in the analysis) was ranked separately for each of the four measurements, with patients showing the least sensitivity in each case being ranked "1". The correlative results are set forth in Table II, and as can readily be seen, a positive statistical correlation exists between the test method of the present invention and the known methods in common use for allergy sensitivity diagnosis.

TABLE II

| TESTS COMPARED | SPEARMAN COEFFICIENT OF RANK CORRELATION | P VALUE |
|---|---|---|
| % BTA vs. Skin Prick Test | 0.57 | <0.0001 |
| % BTA vs. RAST | 0.63 | <0.0001 |
| % BTA vs. Allergen-Induced Histamine Release | 0.46 | <0.001 |
| Allergen-Induced Histamine Release vs. RAST | 0.52 | <0.0005 |

The data shown in Table II indicate that allergic sensitivity can be measured by a reduction in bleeding time, and this diagnosis correlates well with results obtained using routine diagnostic tests, i.e. skin prick testing, RAST and allergen-induced histamine release. Additionally, bleeding time measurement (i.e., hemostasis time) does not suffer from the drawbacks of skin prick testing, e.g. patient discomfort, patient risk, and the difficulties of conducting the test with children.

What is claimed is:

1. A method for determining the allergic sensitivity of a mammal which comprises the steps of contacting a sample of blood from said mammal with an allergen in the presence of a blood clotting inhibitor, measuring the time required for hemostasis of said sample, contacting a sample of blood from said mammal with a clotting inhibitor in the absence of said allergen and measuring the time required for hemostasis in said sample, and determining the difference in time required for hemostasis whereby the sensitivity to said allergen is determined.

2. A method as claimed in claim 1 wherein the allergen is bound to an inert carrier.

3. A method as claimed in claim 1 wherein the allergen is selected from the group consisting of penicillin, Candida albicans, insulin, ovalbumin, lactalbumin, secale, bermuda grass pollen, timothy grass pollen, cocksfoot grass pollen, combinations of grass pollens, ragweed pollen, ragweed antigen E, birch tree pollen, bee venom, snake venom, horse dander, cat epithelium, dog epithelium, haddock, cod, house dust mite, Chrysanthemum leucanthemum, Alternaria tenuis, trypsin, chymotrypsin, dry rot, baker's yeast, tetanus toxoid, diptheria toxin, or ficin.

4. A method as claimed in claim 3 wherein the allergen is a grass pollen.

5. A method as claimed in claim 1 wherein the clotting inhibitor is selected from the group consisting of heparin, sodium citrate, calcium citrate, calcium oxalate, sodium oxalate, and ethylenediamine tetraacetic.

6. A method as claimed in claim 5 wherein the clotting inhibitor is heparin.

* * * * *